(12) United States Patent
Honbo et al.

(10) Patent No.: US 8,668,382 B2
(45) Date of Patent: Mar. 11, 2014

(54) METHOD FOR EVALUATING LIFE OF CABLE INSULATING COATING MATERIAL

(75) Inventors: Kyoko Honbo, Hitachinaka (JP); Motoko Harada, Hitachi (JP); Hideto Momose, Hitachiota (JP); Takanori Yamazaki, Mito (JP); Daisuke Abe, Hitachi (JP); Yoshiaki Nakamura, Hitachi (JP)

(73) Assignee: Hitachi Metals, Ltd., Tokyo (JP)

( * ) Notice: Subject to any disclaimer, the term of this patent is extended or adjusted under 35 U.S.C. 154(b) by 190 days.

(21) Appl. No.: 13/396,199

(22) Filed: Feb. 14, 2012

(65) Prior Publication Data

US 2012/0213246 A1    Aug. 23, 2012

(30) Foreign Application Priority Data

Feb. 23, 2011 (JP) ................. 2011-036574

(51) Int. Cl.
*G01N 3/60* (2006.01)
*G01N 17/00* (2006.01)

(52) U.S. Cl.
USPC .......................................................... 374/57

(58) Field of Classification Search
USPC ........................................................... 374/57
See application file for complete search history.

(56) References Cited

U.S. PATENT DOCUMENTS 4,364,032 A * 12/1982 Narato et al. .................. 377/10
6,852,992 B2    2/2005 Takezawa et al.

FOREIGN PATENT DOCUMENTS

| JP | 3-179245 A | 8/1991 |
|---|---|---|
| JP | 10-96712 A | 4/1998 |
| JP | 10-115601 A | 5/1998 |
| JP | 11-344429 A | 12/1999 |
| JP | 2000-346836 A | 12/2000 |
| JP | 2000346836 A | * 12/2000 |
| JP | 2003-14621 A | 1/2003 |
| JP | 2004-309277 A | 11/2004 |
| JP | 2004-354375 A | 12/2004 |
| JP | 2007-225326 A | 9/2007 |

OTHER PUBLICATIONS

Sagae et al.: The effect of antioxidants on suppression of thermal degradation of insulation material, Collection of Papers for Presentation in IEE Japan National Convention, Mar. 17, 2005, p. 54, including English translation (three (3) pages).
Japanese Office Action dated Mar. 19, 2013 w/ partial English translation (six (6) pages).

(Continued)

*Primary Examiner* — Lisa Caputo
*Assistant Examiner* — Jamel Williams
(74) *Attorney, Agent, or Firm* — Crowell & Moring LLP

(57) ABSTRACT

Disclosed is a method for estimating, within a short time, the life of a cable insulating coating material containing an antioxidant in a suitable concentration based on the rate of decrease of the antioxidant and on the critical concentration of the antioxidant at which oxidative degradation rapidly proceeds. The method tests the coating material to examine its life, the coating material including a base polymer, and an antioxidant having a functional group suppressing an oxidative deteriorative reaction of the base polymer. The method includes performing a thermal degradation test on the coating material; determining the degradation levels and degradation rates of the coating material at two or more time points in the thermal degradation test, based on the ratio of the absorbance of the functional group of the antioxidant to the absorbance of the base polymer; and thereby evaluating the life of the coating material.

13 Claims, 5 Drawing Sheets

(56) References Cited

OTHER PUBLICATIONS

"Degradation of Polymer Materials" with English translation, 1958, pp. 20-22, Corona Publishing Co., Ltd. (nine (9) sheets).

"Practical Encyclopedia of Plastics" with English translation, 1993, pp. 800-807, Industrial Research Center of Japan, Inc. (twenty-seven (27) sheets).

"Report of Technical Research on Countermeasure to Aging (Technical Survey and Research on Evaluating Technologies of Cable Aging for Nuclear Power Plant) in year 2007" with partial English translation, Jun. 2008, Incorporated Administrative Agency: Japan Nuclear Energy Safety Organization (one-hundred-eighty-nine (189) sheets).

* cited by examiner

METHOD FOR EVALUATING LIFE OF CABLE INSULATING COATING MATERIAL

CLAIM OF PRIORITY

The present application claims priority from Japanese patent application serial no. 2011-036574 filed on Feb. 23, 2011, the content of which is hereby incorporated by reference into this application.

FIELD OF THE INVENTION

The present invention relates to methods for evaluating a life of cable insulating coating materials which contain an antioxidant having a radical scavenging function. Specifically, the present invention relates to methods for examining and predicting lives of cable insulating coating materials typically of cables in nuclear power plants.

BACKGROUND OF THE INVENTION

An oxidative degradation phenomenon of a cable insulating coating material is explained typically in "Degradation of Polymer Materials", Corona Publishing Co., Ltd., pages 20-22 (1958) and "Practical Encyclopedia of Plastics", Industrial Research Center of Japan, Inc., pages 800-807 (1993).

In plastics, when a molecular bond of an alkyl group is cleaved by the action of energy typically of heat or light, a radical (R.) is generated. In an environment where oxygen is present, the radical combines with oxygen to form a peroxy radical (ROO.).

R.+O₂→ROO.  (Formula 1)

The peroxy radical is highly reactive, withdraws hydrogen from another molecule, and is converted into a peroxide (ROOH) and a radical (R.).

ROO.+RH→ROOH+R.  (Formula 2)

The newly generated radical (R.) forms another new peroxy radical in the presence of oxygen according to Formula 1. Independently, the peroxide (ROOH) is also unstable and decomposes to form a peroxy radical (ROO.), an oxy radical (RO.), and/or a radical (R.) consequently.

ROOH→RO.+.OH  (Formula 3)

2ROOH→ROO.+RO.+H₂O  (Formula 4)

RO.+RH→ROH+R.  (Formula 5)

As is described above, initially generated one radical (R.) proliferatively forms, via a peroxy radical (ROO.), a multiplicity of new radicals, thus oxidative degradative reactions proceed in a chain. For this reason, cable insulating coating materials requiring a long-term life are added with a radical scavenger as a primary antioxidant so as to suppress oxidative degradative reactions as chain reactions.

Phenolic antioxidants and aromatic amine antioxidants are known as radical scavengers. The phenolic antioxidants prevent the reaction of Formula 2 and thereby prevent the generation of a new radical (R.), in which their phenol group (—OH) gives hydrogen to the peroxy radical and the phenol group itself changes into a stable phenoxy radical (—O.). Such phenol groups are consumed through radical scavenging, but radical chain reactions are suppressed and oxidative degradation is inhibited from proceeding as long as phenol group(s) remains. However, as phenol groups are consumed and depleted, radical scavenging becomes no longer sufficient to suppress radical chain reactions, and this causes oxidative degradation to proceed rapidly.

During proceeding of oxidative degradation, carbonyl groups (C═O) typically of aldehydes, ketones, and carboxylic acids are formed, and, in addition, crosslinking and molecular weight reduction due to cleavage of molecular chain occur. These are described in "Degradation of Polymer Materials", Corona Publishing Co., Ltd., pages 20-22 (1958). Both molecular weight reduction and crosslinking cause the cable insulating coating material to have a lower fracture elongation with respect to tension and thereby cause the cable to reach the end of its life.

For actual evaluation of cable life, tensile tests are widely employed. Some criteria for evaluation or determination of the life have been proposed, while they may vary depending on the type of the cable insulating coating material and the intended use of the cable. For example, Japanese Unexamined Patent Application Publication (JP-A) No. H10-96712 describes a technique on a method for evaluating a cable life in a nuclear power plant. In this technique, the life is defined as the time when a fracture elongation reaches 100% or below. This technique employs a temperature acceleration test for evaluating a long-term life within a short period of time. In this method, lives of samples undergone aging deterioration at two or more different temperatures are plotted as Arrhenius plotting, and a life at an assumed working temperature is determined by extrapolation. According to this technique, the testing duration can be shortened, because degradation is accelerated at higher temperatures, and the sample reaches its life within a short period of time. However, elevation of the testing temperature has a limitation, because degradation reactions and phenomena may change when the testing temperature exceeds a threshold temperature such as melting point or decomposition temperature of a constitutive material, and this causes the slope of the Arrhenius plot to vary.

The fracture elongation in a life test of a cable insulating coating material added with an antioxidant tends to little decrease for the time being and to abruptly decrease toward the end of life. This is because proceeding of oxidative degradation is suppressed while the antioxidant is consumed, but thereafter the antioxidant is exhausted and becomes failing to scavenge radicals sufficiently, and oxidative degradation rapidly proceeds through chain reactions.

As a technique for evaluating degradation of a cable member by a method other than tensile tests, Japanese Unexamined Patent Application Publication (JP-A) No. 2000-346836 discloses a method for determining whether the cable member reaches the end of its life or not based on measurements such as an absorbance ratio measured using a Fourier transform infrared spectrophotometer, an oxidation lag phase measured using a differential scanning calorimeter, and a thermal decomposition starting temperature measured using a thermogravimeter.

In life evaluation of a cable insulating coating material having a long service life, reduction in evaluation time by elevating the testing temperature has a limitation even when a temperature acceleration test is employed, because a straight-line approximation is not established at excessively elevated temperatures, as is described above. Typically, wires (electric wires) for use in nuclear power plants being operated over a long term and playing an important role in the entire society have to have reliability over a longer period of time than wires for general machinery and wires for outside wiring each requiring a not-so-long service life. According to conventional techniques, it takes a long time to perform a life evaluation test on these wires even when the test is a temperature acceleration test.

Such wires and cables in nuclear power plants will be described with reference to FIG. 1. As illustrated in FIG. 1, various control/instrumentation cables 2, power cables 3, and electrical conduits 8 are laid out in a reactor container 1, and these are passed through a container electric penetration assembly 10, are supported by an electrical conduit 5 or a cable tray 4 provided outside of the reactor container, and are connected typically to a controller 7, a central control panel 6, and/or a dose meter 9. These cables are said to measure from about 1000 to about 2000 km in full length. It is considered that a life span necessary for cables in nuclear power plants is about 60 years, but rapid evaluation and prediction of the life of cables is still required, as is described above.

In addition, when life evaluation based on the fracture elongation in a tensile test is adopted to a cable insulating coating material containing an antioxidant, reduction in fracture elongation is not remarkable until the antioxidant is exhausted, and, as a result, evaluation should be continued to the end of the life. Owing also to this, it takes a long time to evaluate the life of the coating material.

It may be also possible to employ, as an index for degradation, not the fracture elongation, but another measurement such as an absorbance ratio measured using a Fourier transform infrared spectrophotometer, an oxidation lag phase measured using a differential scanning calorimeter, or a thermal decomposition starting temperature measured using a thermogravimeter, as in the technique disclosed in Japanese Unexamined Patent Application Publication (JP-A) No. 2000-346836. However, the technique disclosed in the patent literature uses the measurement as an index for determining whether the tested material reaches the end of its life or not by comparing the measurement with a threshold, and the threshold used as a criterion is determined from a measurement of a sample undergone long-term degradation. The technique is therefore effective for helping the evaluation to have higher precision and for simplifying the test. However, the literature fails to refer to shortening of the evaluation period including the determination of the threshold used as a criterion.

Japanese Unexamined Patent Application Publication (JP-A) No. H10-96712 discloses a technique as a method for diagnosing a degradation level of a cable insulating coating layer. In this technique, light is applied to the insulating coating layer (insulating coating material) to generate sound due to photoacoustic effect; based on the sound, degree of oxidation, degree of hardening, and degree of radiation degradation, for example, of the insulating coating material are evaluated, and thereby the degradation level of the cable insulating coating material is evaluated.

Japanese Unexamined Patent Application Publication (JP-A) No. H10-115601 discloses a method for diagnosing the degradation level of a cable insulating coating material by applying light to the cable insulating coating material, detecting the oscillation of elastic body (elastic waves) propagating through the insulating coating material with a sensor, and analyzing the oscillation.

The degradation mechanism of a crosslinked polyethylene widely used as an cable insulating coating material in nuclear power plants, and the action of an antioxidant will be illustrated with reference to FIG. 2. The crosslinked polyethylene gives a radical (—$CH_2$—CH.) in a radiation environment, and this radical is converted into a peroxy radical (—$CH_2$OO.) and thereby cleaves the principal chain of the polyethylene. A terminal hydroxyl (OH) of the antioxidant scavenges the peroxy radical and thereby suppresses the cleavage of the principal chain of the polyethylene.

An object of the present invention is to provide a technique for estimating, within a short time, a life of a cable insulating coating material having a long service life.

SUMMARY OF THE INVENTION

The present invention provides, in an aspect, a method for testing a cable insulating coating material to evaluate a life thereof, the cable insulating coating material being used for covering a conductor and including a base polymer and an antioxidant having a functional group for suppressing an oxidative deteriorative reaction of the base polymer, the method comprising the steps of performing a thermal degradation test on a cable insulating coating material containing the antioxidant; determining degradation levels and degradation rates of the cable insulating coating material at two or more time points in the thermal degradation test based on a ratio of an absorbance of the functional group of the antioxidant to an absorbance of the base polymer; and evaluating the life of the cable insulating coating material.

The present invention enables short-time predication of the life of a cable insulating coating material. This is because, according to the present invention, the concentration of a functional group having a radical scavenging function in the molecular structure of an antioxidant is quantitatively determined based on a ratio of an absorbance of the functional group to an absorbance of the base polymer; and the degradation level of the cable insulating coating material is evaluated based on the degradation rate of the cable insulating coating material and the amount of the functional groups remained therein. As a result, the present invention benefits improvements in reliability and safety typically of wiring systems in nuclear power plants requiring very long lives.

Figure 1:
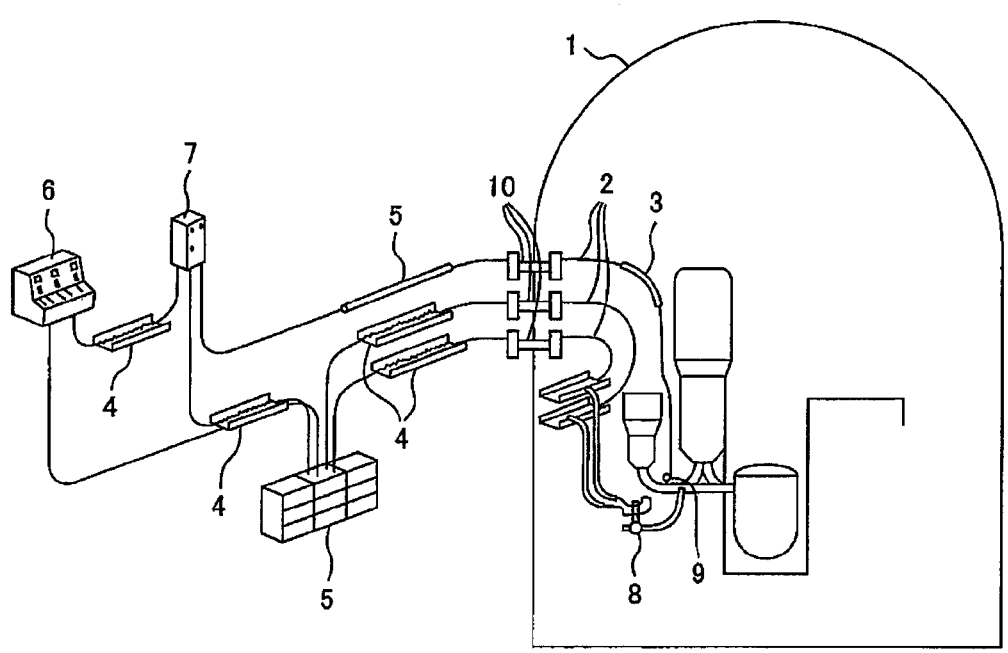
FIG. 1 is a schematic diagram illustrating how cables and other parts are arranged in a nuclear power plant to which the present invention is applied.
Figure 2:
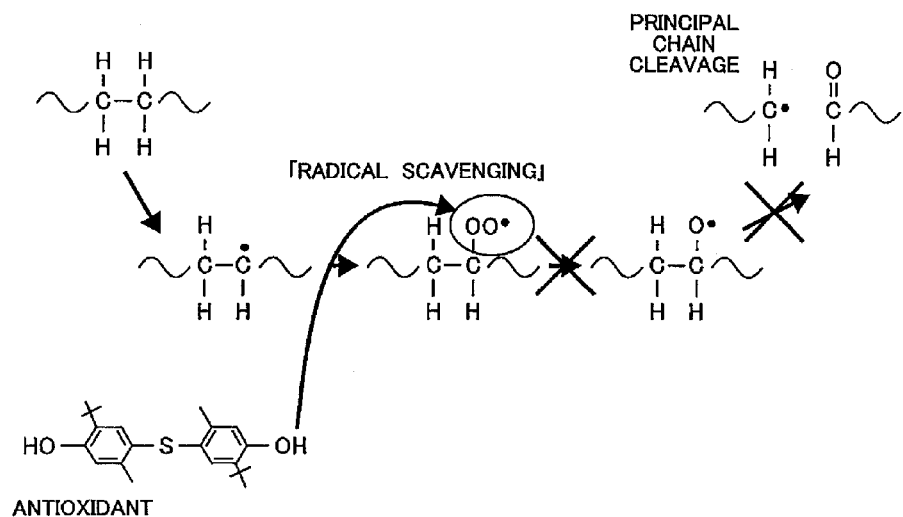
FIG. 2 is a diagram illustrating the degradation mechanism of a crosslinked polyethylene used as a cable insulating coating material to which the present invention is applied; and the degradation prevention mechanism of an antioxidant.

Reference signs in FIGS. 4 to 9 are defined as follows.

11: degradation-time dependence of fracture elongation

12: degradation-time dependence of absorbance ratio of phenol group in an antioxidant (initial concentration: 0.15 percent by weight)

13: degradation-time dependence of absorbance ratio of phenol group in an antioxidant (initial concentration: 0.2 percent by weight)

14: peak derived from phenol group of the antioxidant in an infrared spectrum as measured after subjecting a sample having an initial antioxidant concentration of 0.2 percent by weight to a thermal degradation test at 120° C. for 400 hours

15: peak of C—H bending vibration of the base polymer in an infrared spectrum as measured after subjecting a sample having an initial antioxidant concentration of 0.2 percent by weight to a thermal degradation test at 120° C. for 400 hours

16: distribution of absorbance ratio of phenol group in a thickness direction of a cable coating before degradation

17: distribution of absorbance ratio of phenol group in a thickness direction of the cable coating after 400-hour thermal degradation

18: distribution of absorbance ratio of phenol group in a thickness direction of the cable coating after 800-hour thermal degradation

19: distribution of absorbance ratio of phenol group in a thickness direction of the cable coating after 1600-hour thermal degradation

20: distribution of absorbance ratio of phenol group in a thickness direction of the cable coating after 3200-hour thermal degradation

21: plot and extrapolation line of lifetime of a sample containing an antioxidant in a concentration of 0.15 percent by weight at 120° C., 110° C., and 100° C.

22: expected life of the sample containing the antioxidant in a concentration of 0.15 percent by weight at an assumed working temperature of 60° C., which life is read out from the extrapolation line

23: plot and extrapolation line of lifetime of a sample containing the antioxidant in a concentration of 0.2 percent by weight at 120° C., 110° C., and 100° C.

24: expected life of the sample containing the antioxidant in a concentration of 0.2 percent by weight at an assumed working temperature of 60° C., which life is read out from the extrapolation line

DETAILED DESCRIPTION OF THE PREFERRED EMBODIMENTS

As used herein the phrase "evaluation of the life of a cable insulating coating material" refers not to determining whether the cable insulating coating material actually degrades and reaches the application limit but to prediction of the life (application limit) of the cable insulating coating material, and this technique is clearly distinguished from techniques for detecting or computing the life span (boundary life).

The present invention enables brief estimation of the life of a cable insulating material (cable coating material) containing a suitable amount of an antioxidant based on the rate of decrease of the antioxidant and on the critical concentration of the antioxidant above which oxidative degradation rapidly proceeds, whereas it takes a long time to perform evaluation of the life of the coating material according to conventional techniques. This enables life estimation within a short time at a not so high degradation test temperature and consequently enables early-stage prediction of the life when life data at two or more different degradation test temperatures are plotted as an Arrhenius plot to evaluate the life at an assumed working temperature. Degradation tests performed in the present invention are accelerated tests and are performed at temperatures higher than temperatures to which an actual coated cable is exposed.

Exemplary embodiments of the present invention are as follows.

(1) In an embodiment, the method for testing a cable insulating coating material to evaluate a life thereof includes the steps of performing thermal degradation tests on a cable insulating coating material containing the antioxidant in an initial concentration lower than an actual-use initial concentration (practical concentration intended to achieve a predetermined life) and on a cable insulating coating material containing the antioxidant in the actual-use initial concentration; determining degradation levels and degradation rates of the cable insulating coating materials containing the antioxidant in the respective concentrations based on the ratios of an absorbance of the functional group of the antioxidant in the respective concentrations to an absorbance of the base polymer; and evaluating a life of the cable insulating coating material containing the antioxidant in the actual-use initial concentration.

(2) In another embodiment of the method for testing a cable insulating coating material to evaluate a life thereof, the antioxidant has a functional group having a radical scavenging function in a molecular structure thereof.

(3) In still another embodiment, the present invention provides method for testing a cable insulating coating material to evaluate a life thereof, the cable insulating coating material being used for covering a conductor and including a base polymer and an antioxidant having a functional group for suppressing a deteriorative reaction of the base polymer. The method includes the steps of:

performing a thermal degradation test on a first sample containing the antioxidant in an initial concentration lower than an actual-use initial concentration, and estimating such a critical concentration of the radical-scavenging functional group as to suppress oxidative degradation based on a correlation between a fracture elongation of the first sample in a tensile test and a peak intensity of the radical-scavenging functional group in the first sample;

performing a thermal degradation test on a second sample containing the antioxidant in the actual-use initial concentration, and estimating an initial peak intensity of the radical-scavenging functional group in the second sample and a rate of decrease of the peak intensity; and calculating a time for the concentration of the radical-scavenging functional group in the first sample containing the antioxidant in an initial concentration lower than the actual-use initial concentration to reach the estimated critical concentration, based on the estimated initial peak intensity and rate of decrease of the peak intensity of the radical-scavenging functional group in the second sample containing the antioxidant in the actual-use initial concentration, and predicting a thermal degradation life of the cable coating material at a predetermined temperature.

(4) In yet another embodiment, the present invention provides a method for testing a cable insulating coating material to evaluate a life thereof, the cable insulating coating material including an antioxidant having a functional group for suppressing an oxidative deteriorative reaction. This method includes the steps of:

using means for quantitatively determining a concentration of a functional group having a radical scavenging function in a molecular structure of the antioxidant through infrared spectrophotometry;

performing a thermal degradation test on a first sample containing the antioxidant in an initial concentration lower than an actual-use initial concentration, and estimating such a critical concentration of the radical-scavenging functional group as to suppress oxidative degradation based on a correlation between a fracture elongation of the first sample in a tensile test and a peak intensity of the radical-scavenging functional group in the first sample;

performing a thermal degradation test on a second sample containing the antioxidant in the actual-use initial concentration, and estimating an initial peak intensity of the radical-scavenging functional group in the second sample and a rate of decrease of the peak intensity; and calculating a time for the concentration of the radical-scavenging functional group in the first sample containing the antioxidant in an initial concentration lower than the actual-use initial concentration to reach the estimated critical concentration based on the initial peak intensity and the rate of decrease of the peak intensity of the radical-scavenging functional group each estimated on the second sample containing the antioxidant in the actual-use initial concentration, and predicting a thermal degradation life of the cable insulating coating material at a predetermined temperature.

(5) In another embodiment, the method according to (4) may further include the steps of collecting data of concentration distribution of the radical-scavenging functional group in a thickness direction of cable insulating coating through an infrared spectral mapping measurement of the concentration of the radical-scavenging functional group in a molecular structure of the antioxidant; and performing estimation of the concentration and the critical concentration of the functional group also in consideration of a pattern of the concentration distribution.

(6) In still another embodiment, the present invention provides a method for testing a cable insulating coating material to evaluate a life thereof, the method comprising the steps of evaluating a life at an assumed working temperature through Arrhenius plotting of thermal degradation lives at two or more different temperatures; and adopting, to all or part of the thermal degradation lives, a thermal degradation life or lives predicted by the life evaluation method according to (4).

(7) The present invention provides, in yet another embodiment, a method for testing a cable insulating coating material to evaluate a life thereof, the cable insulating coating material including a base polymer and an antioxidant for suppressing an oxidative deteriorative reaction, the method comprising the steps of:

using means for quantitatively determining a concentration of a functional group having a radical scavenging function in a molecular structure of the antioxidant based on a ratio of an absorbance of the functional group to an absorbance of the base polymer each obtained through infrared spectrophotometry; as a first stage, preparing a first sample containing the antioxidant in an initial concentration lower than an actual-use initial concentration, performing a thermal degradation test on the first sample, and estimating such a critical concentration of the radical-scavenging functional group as to suppress oxidative degradation based on a correlation between a change in fracture elongation of the first sample with a heating time, the fracture elongation being determined in a tensile test and a change in peak intensity of the radical-scavenging functional group with a heating time; as a second stage, preparing a second sample containing the antioxidant in a concentration intended to achieve a target life, performing a thermal degradation test on the second sample, and estimating a rate of decrease of the radical-scavenging functional group; checking that the rates of decrease of the radical-scavenging functional group estimated in the first stage and the second stage, respectively, are equal to each other; calculating a time for the concentration of the radical-scavenging functional group in the second stage to reach the critical concentration estimated in the first stage, based on a difference in concentration of the radical-scavenging functional group between the first stage and the second stage at an identical degradation time and based on the estimated rate of decrease of the radical-scavenging functional group; and predicting a thermal degradation life of the cable insulating coating material at a temperature used in the thermal degradation test.

(8) In another embodiment, the life testing method according to (7) further includes the steps of performing an infrared spectrophotometric mapping measurement of the concentration of the radical-scavenging functional group in the molecular structure of the antioxidant; collecting data of concentration distribution of the radical-scavenging functional group in a thickness direction of cable insulating coating; and calculating the concentration of the functional group based on an average of the concentration distribution while excluding data showing an irregularity in a distribution pattern from calculations performed in the estimations of the concentration and rate of decrease of the peak intensity of the radical-scavenging functional group, and subjecting the results to the prediction of the life.

(9) In another embodiment, the present invention provides a method for testing a cable insulating coating material to evaluate a life thereof, the cable coating material including an antioxidant for suppressing an oxidative deteriorative reaction. The method includes the steps of evaluating a life of the cable coating material at an assumed working temperature through Arrhenius plotting of thermal degradation lives at two or more different temperatures; and adopting, to all or part of the thermal degradation lives, a thermal degradation life or lives predicted by the life evaluation method according to (8).

(10) In another embodiment, the present invention provides a method for testing a cable insulating coating material for use in a nuclear power plant to evaluate a life thereof, the cable insulating coating material being used for a cable in an electrical facility in the nuclear power plant and including a base polymer and an antioxidant, the antioxidant containing a functional group having a radical scavenging function. The method includes the steps of using means for quantitatively determining a concentration of the radical-scavenging functional group in a molecular structure of the antioxidant based on a ratio of an absorbance of the functional group to an absorbance of the base polymer each obtained through infrared spectrophotometry;

as a first stage, preparing a first sample containing the antioxidant in a concentration lower than an actual-use initial concentration, performing a thermal degradation test on the first sample, and estimating such a critical concentration of the radical-scavenging functional group as to suppress oxidative degradation based on a correlation between a change in fracture elongation of the first sample with a heating time, the fracture elongation being determined in a tensile test and a change in peak intensity of the radical-scavenging functional group with a heating time; as a second stage, preparing a second sample containing the antioxidant in a concentration intended to achieve a target life, performing a thermal degradation test on the second sample, and estimating a rate of decrease of the radical-scavenging functional group; checking that the rates of decrease of the radical-scavenging functional group estimated in the first stage and the second stage, respectively, are equal to each other; calculating a time for the concentration of the radical-scavenging functional group in the second stage to reach the critical concentration estimated in the first stage, based on a difference in concentration of the radical-scavenging functional group between the first stage and the second stage at an identical degradation time and based on the estimated rate of decrease of the radical-scavenging functional group; and predicting a thermal degradation life of the cable insulating coating material at a temperature used in the thermal degradation test.

(11) In another embodiment, the life testing method according to (10) further includes the steps of performing an infrared spectrophotometric mapping measurement of the concentration of the radical-scavenging functional group in the molecular structure of the antioxidant; collecting data of concentration distribution of the radical-scavenging functional group in a thickness direction of cable coating; and calculating the concentration of the functional group based on an average of the concentration distribution while excluding data showing an irregularity in a distribution pattern from calculations performed in the estimations of the concentration and rate of decrease of the peak intensity of the radical-scavenging functional group, and subjecting the results to the prediction of the life.

(12) In yet another embodiment, the present invention provides a method for testing a cable insulating coating material for use in a nuclear power plant to evaluate a life thereof, the method comprising the steps of:

evaluating a life of the cable insulating coating material at an assumed working temperature through Arrhenius plotting of thermal degradation lives at two or more different temperatures; and adopting, to all or part of the thermal degradation lives, a thermal degradation life or lives predicted by the life evaluation method according to (10).

The present inventors performed the quantitative analysis of an antioxidant in a cable insulating coating material upon a thermal degradation test using a Fourier transform infrared spectrophotometer and obtained the following findings on life estimation.

1) The antioxidant in a sample heated at a given temperature decreases at an approximately constant rate.

2) The degradation of the sample rapidly proceeds at the point of time when the antioxidant decreases to a certain concentration or less, and the sample reaches the end of its life.

Based on these findings, the present inventors have found that the following procedural steps enable life prediction within a short time.

Step 1: While using means for quantitatively determining a concentration of a functional group having a radical scavenging function in a molecular structure of the antioxidant through infrared spectrophotometry, as a first stage, performing a thermal degradation test on a first sample containing the antioxidant in an initial concentration lower than the actual-use initial concentration; and estimating such a critical concentration of the radical-scavenging functional group as to suppress oxidative degradation, based on a correlation between a fracture elongation of the first sample in a tensile test and a peak intensity of the radical-scavenging functional group. The critical concentration herein is defined as a concentration of the antioxidant at the time when the sample reaches the end of its life, in which the time is determined based on the results of the tensile test. The amount (concentration) of the antioxidant in Step 1 should be lower than a concentration set as intended to achieve a target life. With decrease in concentration of the antioxidant, the degradation proceeds in earlier stages. However, the antioxidant is consumed partly upon the manufacturing of the cable, and the antioxidant, if contained in an excessively low initial concentration, is all but consumed before the thermal degradation test is performed. This impedes precise evaluation of the critical concentration and the rate of decrease of the antioxidant. For these reasons, this step is preferably tried using samples containing the antioxidant in several different concentrations.

Step 2) Performing a thermal degradation test on a second sample containing the antioxidant in a concentration set being intended to achieve the target life, and estimating the initial peak intensity of the radical-scavenging functional group and the rate of decrease of the peak intensity.

Step 3) Calculating a time for the concentration to reach the critical concentration estimated in the first stage, the calculation being based on the initial peak intensity of the radical-scavenging functional group and the rate of decrease of the peak intensity estimated in Step 2, and thereby predicting the thermal degradation life of the cable insulating coating material at a heat test temperature.

Upon estimation of the critical concentration and upon estimation of the rate of decrease of the antioxidant, it is accepted that tests are performed on two or more samples, the results are averaged, and the average is used in the estimations. In addition, the present inventors made mapping measurements, which give two-dimensional absorbance distributions, in Fourier transform infrared spectrometry to evaluate the absorbance distribution of the radical-scavenging functional group in a cross section in the thickness direction of the cable coating. As a result, they have found that the concentration of the antioxidant has some distribution. In this connection, the concentration of the antioxidant affects the suppression of oxidative degradation. Based on these findings, the present inventors have further found that the life can be estimated with a higher accuracy by collecting data about the concentration distribution of the radical-scavenging functional group in the thickness direction of the cable coating, and calculating the concentration of the functional group and the critical concentration in consideration also of the distribution pattern.

A life at an arbitrary thermal degradation temperature can be predicted according to the above procedural steps. A life at an assumed working temperature can be determined by performing life prediction at two or more different thermal degradation temperatures, plotting the results as an Arrhenius plot, and determining the life through extrapolation. According to the present invention, the time period to collect data to be subjected to Arrhenius plotting can be shortened, and, as a result, the time period to predict the life can be shortened.

Cable insulating coating material samples for evaluation were prepared by adding dicumyl peroxide as a crosslinking agent and 4,4-thiobis(6-tert-butyl-3-methylphenol) as an antioxidant to a polyethylene, kneading them with each other, and performing a crosslinking treatment at 180° C. Thus, samples containing the phenolic antioxidant in concentrations of 0.15 percent by weight and 0.20 percent by weight, respectively, were prepared as working examples.

Using these materials, accelerated degradation tests were performed in a forced draft circulating thermostat by a method in accordance with Japanese Industrial Standards K7212. The thermal degradation temperature was 120° C.

A series of samples were subjected to the tests simultaneously, were retrieved after lapses of 400 hours, 800 hours, 1600 hours, and 3200 hours, respectively, the retrieved samples were cut into 600-μm thick sections in a direction perpendicular to the sample surface using a microtome, and the sections were subjected to spectrophotometry using a Fourier transform infrared spectrophotometer. The Fourier transform infrared spectrophotometer used herein was a system capable of performing microscopic imaging measurements.

In the phenolic antioxidant, a phenol group (—OH) in the molecular structure scavenges a peroxy radical causing chain reactions of oxidative degradation and, in this process, the phenol group itself irreversibly changes into another structure. For this reason, the phenol groups are consumed, and the concentration thereof decreases with peroxy radical scavenging, and, along with this, the peak in infrared spectrum derived from phenol group becomes small.

An absorption peak of OH stretching vibration of phenol group in the antioxidant was detected at $3510\ cm^{-1}$. The ratio of the peak absorbance to the absorbance of a peak of CH in-plane bending vibration of the polyethylene in the base polymer observed at $1300\ cm^{-1}$ was taken, and thus the concentration of unconsumed phenol groups of the antioxidant was evaluated. The ratio is taken to the peak of the base polymer for the purpose of collecting the influence of variation in thickness of measurement samples. The ratio is taken in absorbance because the absorbance is proportional to the sample thickness and the concentration of the functional group.

To detect a peak of the antioxidant when contained in a low concentration, the sample should have a somewhat large thickness. If the sample has an excessively large thickness, however, some of absorption peaks of the base polymer necessary for the correction may have saturated absorbances due to excessively large absorption and may fail to be evaluated accurately. In addition, such a sample having an excessively large thickness may cause inferior spatial resolution upon imaging measurements because of spreading infrared rays in the sample. For these reasons, an optimum sample thickness should be employed in consideration typically of the antioxidant concentration and the intensity of a peak to be measured.

A peak derived from CH stretching vibration observed at wavenumbers of from 3000 to $2800\ cm^{-1}$ is generally used as a base peak of polyethylene. In the working examples, however, the samples have large thicknesses of 600 μm so as to detect a peak of the antioxidant contained in an initial concentration lower than the actual-use initial concentration, thereby the peak of CH stretching vibration is saturated. Accordingly, the absorbance ratio was calculated with respect to an unsaturated peak of CH in-plane bending vibration observed at $1300\ cm^{-1}$.

Figure 4:
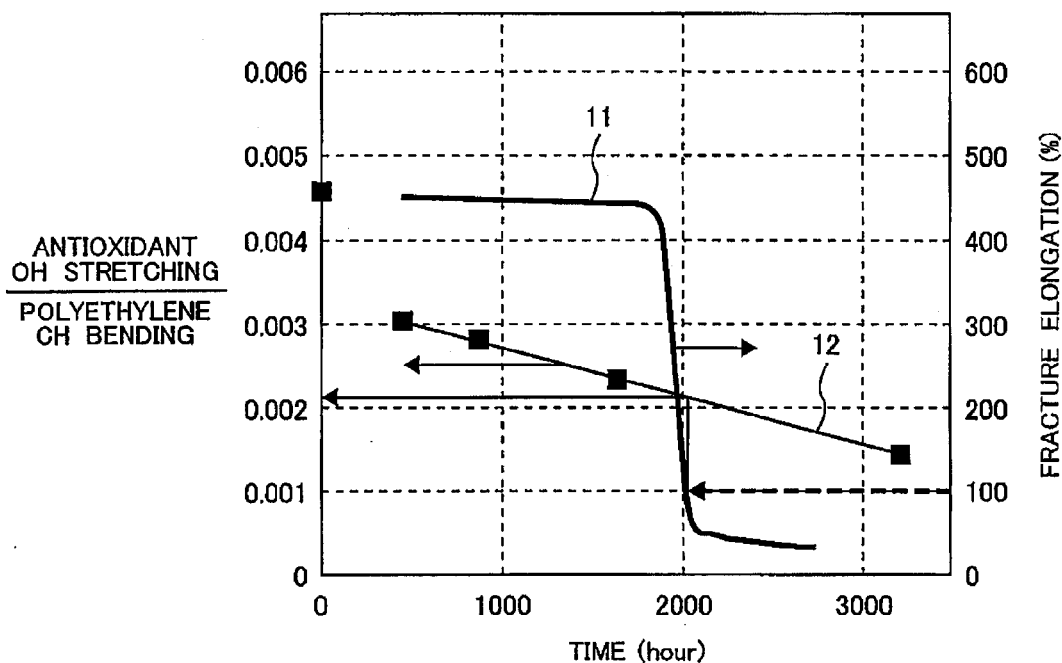
FIG. 4 is a graph illustrating how the fracture elongation and the antioxidant concentration vary depending on the degradation time in a thermal degradation test at 120° C. of a cable insulating coating material having an initial antioxidant concentration of 0.15 percent by weight.

FIG. 4 is a graph illustrating how the fracture elongation 11 of the cable insulating coating material prepared by the above procedure steps and having an antioxidant concentration of 0.15 percent by weight and the absorbance ratio 12 of phenol group of the antioxidant vary respectively depending on the degradation time in an accelerated degradation test at 120° C.

As the absorbance of phenol group, an average absorbance in the vicinity of the surface (in a region with depths of from 100 to 300 μm from the surface) obtained in the imaging measurement was used. The absorbance ratio of phenol group decreases at a certain rate with the degradation time. This is because phenol groups are consumed by supplying hydrogens to peroxy radicals generated in the oxidative degradation test (accelerated degradation test) to thereby stabilize the peroxy radicals and suppress radical chain reactions.

In contrast, the fracture elongation does not show significant decrease up to a degradation time near to 2000 hours but abruptly decreases to 100% of the life evaluation criteria at a degradation time of about 2000 hours. The absorbance ratio of phenol group at 2000 hours, at which the fracture elongation reaches 100%, is estimated as 0.0022 based on the plot of the absorbance ratio 12 in FIG. 4, and this is defined as the critical concentration of the material having the composition in this working example in the thermal degradation test at 120° C. Estimation of the critical concentration can be performed with more precisely by determining the fracture elongation and the absorbance ratio of phenol group at respective degradation time points on two or more samples, plotting averages of the determined results, or subjecting the averages to functional approximation, so as to cancel or reduce effects of variations.

The critical concentration varies depending typically on the molecular weight of the base polymer, the type of the antioxidant, and the thermal degradation test temperature. Accordingly, when the combination of materials or the thermal degradation test temperature is changed, a new critical concentration should be determined according to the above-mentioned method.

To determine the critical concentration within a further shorter time, the test may be performed using a sample containing the antioxidant in an initial concentration lower than the actual-use initial concentration. However, when the sample is prepared by chemical crosslinking using a crosslinking agent, the antioxidant works as a radical scavenger also upon radicals generated by the crosslinking agent and is thereby consumed, and thus, phenol groups have already decreased at the time when the thermal degradation test is initiated. For this reason, the antioxidant, if contained in an excessively low initial concentration, may reach its critical concentration in a stage before the degradation test, and this may impede the detection of the rate of decrease (rate of consumption) of the antioxidant. The amount (initial concentration) of the antioxidant should be determined to avoid this.

Figure 5:
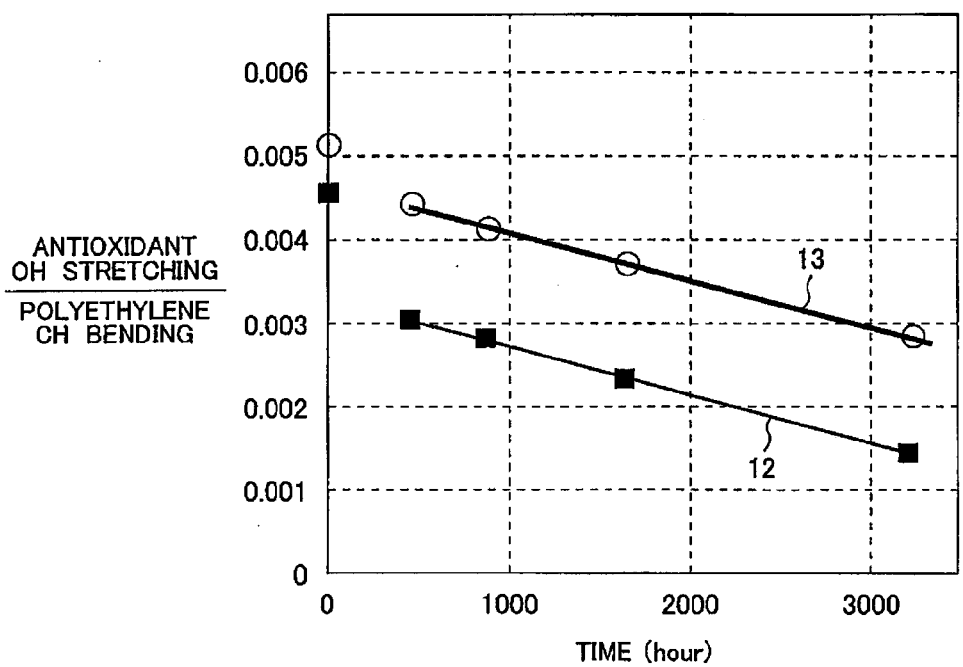
FIG. 5 is a graph illustrating how the phenol group concentration varies depending on the degradation time in a thermal degradation test at 120° C., for comparison between cable insulating coating materials having initial phenolic antioxidant concentrations of 0.15 percent by weight and 0.2 percent by weight, respectively.

FIG. 5 is a graph illustrating how the absorbance ratio of phenol group varies depending on the degradation time in a degradation test at 120° C., for comparison between the cable insulating coating material containing the phenolic antioxidant in an initial concentration of 0.15 percent by weight and the cable coating material containing the phenolic antioxidant in an initial concentration of 0.2 percent by weight.

Both the absorbance ratio of phenol group in the sample having an initial antioxidant concentration of 0.2 percent by weight and the absorbance ratio of phenol group in the sample having an initial antioxidant concentration of 0.15 percent by weight decrease at a constant rate, and based on this, the amounts of phenol group consumed per time are assumed to be almost equal to each other. There is a difference in absorbance ratio of about 0.0014 between the sample having an initial antioxidant concentration of 0.2 percent by weight and the sample having an initial antioxidant concentration of 0.15 percent by weight, but the two samples have amounts of consumed phenol groups per 1000 hours of both about 0.00054. Accordingly, the difference in time for the antioxidant to reach the critical concentration is estimated to be about 2590 hours between the sample having an initial antioxidant concentration of 0.2 percent by weight and the sample having an initial antioxidant concentration of 0.15 percent by weight. Specifically, a time for the sample having an initial antioxidant concentration of 0.2 percent by weight to have an absorbance ratio of phenol group of 0.0025 corresponding to the critical concentration is estimated to be 4590 hours. Thus, the life of a sample containing antioxidant in a high concentration can be roughly estimated by estimating the critical concentration of phenol group in the antioxidant so as to suppress radical chain reactions on another sample containing the antioxidant in an initial concentration lower than the actual-use initial concentration and checking that the consumption rate of phenol group is identical even in the sample having a high antioxidant concentration.

Figure 6:
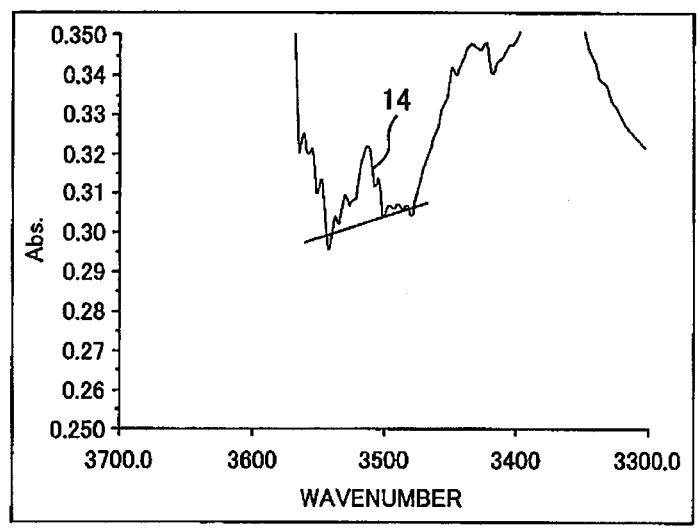
FIG. 6 depicts a spectrum in the vicinity of a peak derived from phenol group, which spectrum is obtained by subjecting a cable insulating coating material having an initial phenolic antioxidant concentration of 0.2 percent by weight to a thermal degradation test at 120° C., retrieving the cable coating material at a lapse of 400 hours, and subjecting the coating material to an infrared spectrometry.
Figure 7:
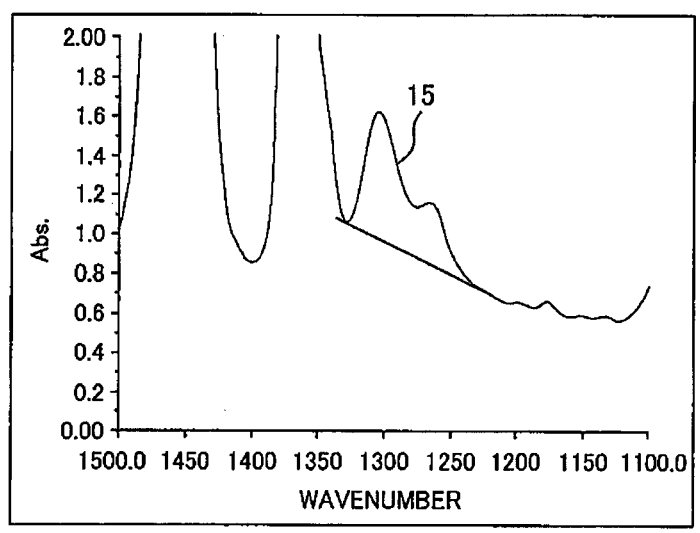
FIG. 7 depicts a spectrum in the vicinity of a peak of C—H bending vibration of a base polymer, which spectrum is obtained by subjecting a cable insulating coating material having an initial phenolic antioxidant concentration of 0.2 percent by weight to a thermal degradation test at 120° C., retrieving the cable coating material at a lapse of 400 hours, and subjecting the coating material to an infrared spectrometry.

FIGS. 6 and 7 depict exemplary measured infrared spectra both of which are absorbance spectra of the sample having an initial antioxidant concentration of 0.2 percent by weight in a thermal deterioration test at 120° C. after a lapse of 400 hours.

FIG. 6 is an enlarged view of a region at wavenumbers of around 3500 $cm^{-1}$, in which a peak 14 is observed at 3510 $cm^{-1}$ which peak is assigned to OH stretching vibration of radical-scavenging phenol group of the antioxidant. FIG. 7 is an enlarged view of a region at wavenumbers of around 1300 $cm^{-1}$, in which a peak 15 is observed at 1300 $cm^{-1}$ which peak is assigned to CH in-plane bending vibration of the base polymer polyethylene. The quantity of phenol group was determined based on the ratio of the absorbance of the peak 14 to the absorbance of the peak 15.

Figure 8:
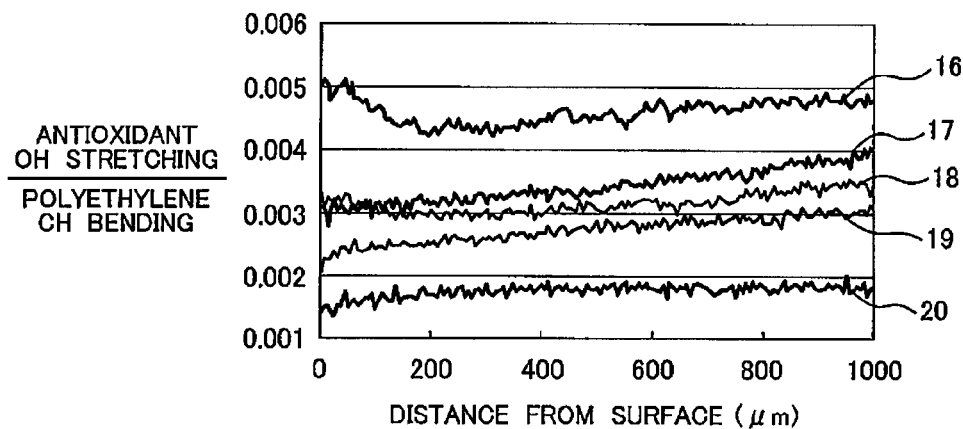
FIG. 8 is a graph illustrating how the absorbance ratio of phenol group distributes in a thickness direction of cable coating at various degradation time points, as determined from imaging measurements.

FIG. 8 depicts a graph illustrating distributions of the absorbance ratio of phenol group in a thickness direction of the cable coating at respective degradation time points, as determined from the mapping measurements. The reference sign 16 stands for the distribution before degradation, i.e., at a degradation time of 0 hour, and the reference signs 17, 18, 19, and 20 stand for the distributions at degradation time points of 400 hours, 800 hours, 1600 hours, and 3200 hours, respectively.

The data demonstrate that the concentration of phenol group is high in the vicinity of the outermost surface layer in the distribution at a degradation time of 0 hour, indicating that this is probably because the antioxidant is enriched in the surface layer upon the preparation of the sample. In contrast, the distributions at degradation time points of 400 hours, 800 hours, 1600 hours, and 3200 hours show an identical tendency that the concentration of phenol group decreases from the inside toward the surface. These results indicate that only the distribution at a degradation time of 0 hour is in another pattern.

In the plots of the absorbance ratio of phenol group in FIGS. 4 and 5, the points (data) at a degradation time of 0 hour are apparently out of the linear relation of the points at degradation time points of 400 hours or later and impede the estimation of the rate of decrease. These data were excluded from data for estimation of the rate of decrease in consideration also of the specific distribution pattern at the degradation time of 0 hour as indicated in FIG. 8.

A working example of life estimation at a degradation temperature of 120° C. has been described above. Life estimations at lower degradation temperatures of, for example, 110° C. and 100° C. are also possible, and a life at an assumed working temperature can be estimated by subjecting the estimated lives at these degradation temperatures to Arrhenius plotting.

Figure 9:
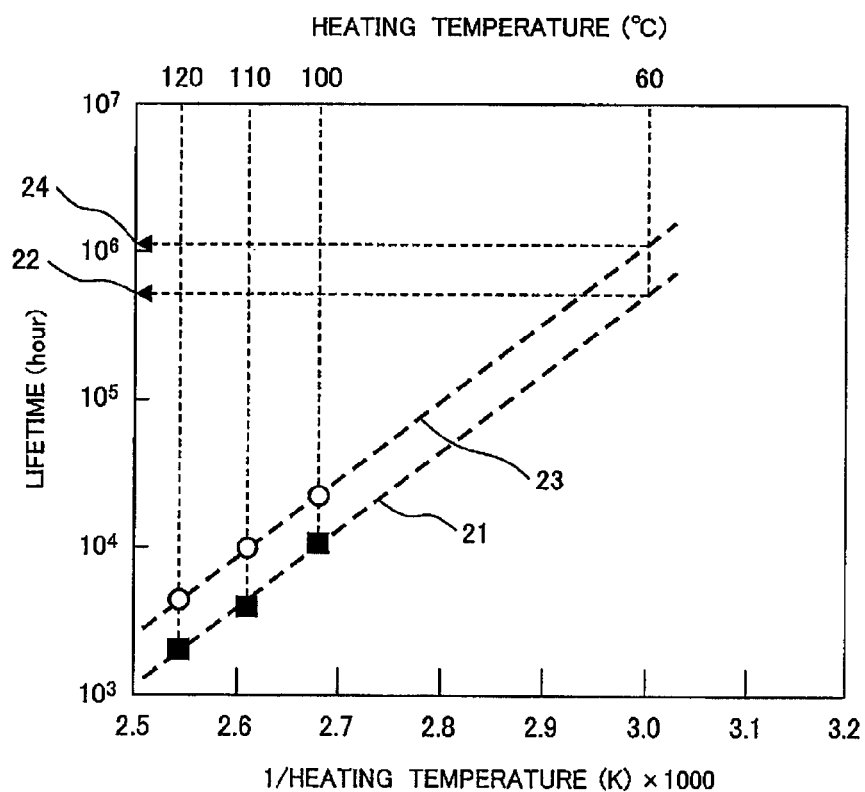
FIG. 9 depicts an exemplary evaluation of the life of a coating material through Arrhenius plotting based on data obtained in accelerated thermal degradation tests.

FIG. 9 depicts an exemplary evaluation of a life at an assumed working temperature using Arrhenius plotting based on data obtained in accelerated thermal degradation tests. The reference sign 21 stands for a plot of lifetimes at 120° C., 110° C., and 100° C. and a corresponding extrapolation line in a first sample having an initial antioxidant concentration of 0.15 percent by weight. An expected life of a nuclear power cable at an assumed working temperature, 60° C., in a life test is determined by a Y-coordinate 22 at which the extrapolation line intersects the heating temperature of 60° C. Likewise, the reference sign 23 stands for a plot of lifetimes at 120° C., 110° C., and 100° C. and a corresponding extrapolation line in a second sample having an initial antioxidant concentration of 0.2 percent by weight; and the reference sign 24 stands for an expected life of the second sample at the assumed working temperature of 60° C. Evaluation of lives of the first and second samples having respective antioxidant concentrations at the assumed working temperature can be performed within a short time by determining all or part of plots 21 and 23 at 120° C., 110° C., and 100° C. through the aforementioned estimation of the consumption rate and critical concentration of the antioxidant.

Figure 3:
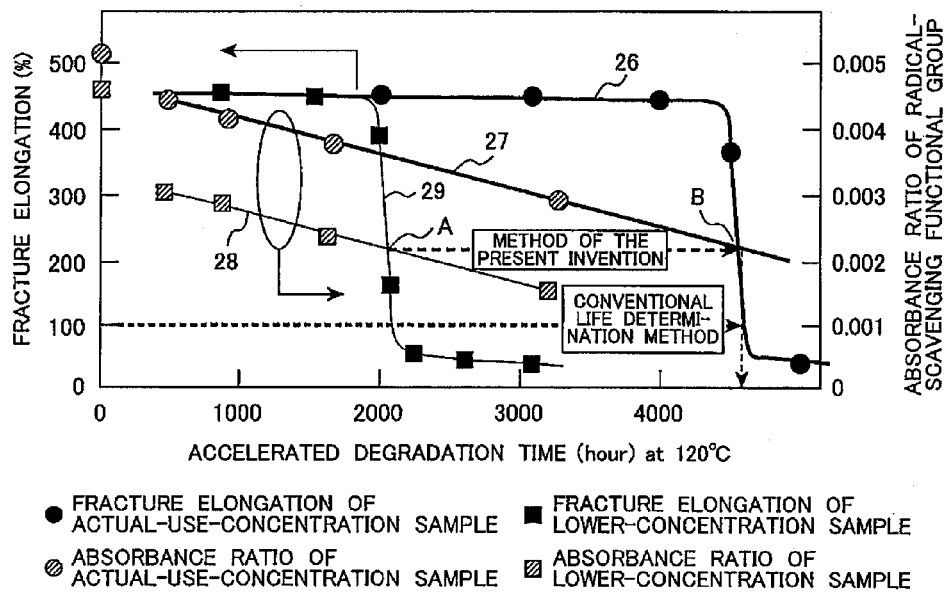
FIG. 3 is a graph illustrating, in accelerated degradation tests of cable insulating coating materials, how the fracture elongation and the absorbance ratio of the radical-scavenging functional group in the antioxidant vary depending on the test time, for comparison between a conventional life evaluation method and a life predicting method according to the present invention.

FIG. 3 illustrates the relation between the fracture elongation of a insulating coating material and the absorbance ratio of the radical-scavenging functional group, for the comparison between the life prediction method according to the present invention using an accelerated test and a conventional life evaluation method using an accelerated test. According to the conventional life evaluation method, for example, the fracture elongation abruptly decreases after a lapse of 2000 hours or longer, and this time is determined as the end of life of the insulating coating material. However, it takes a long time of 2000 hours or longer even for the accelerated test to evaluate the end of life of the insulating coating material. In contrast, according to the method of the present invention, the time at which the fracture elongation reaches a predetermined level (life of the coating material) can be predicted even before a lapse of 2000 hours, because the antioxidant content linearly decreases.

As is illustrated in FIG. 3, the life of a insulating coating material can be predicted by performing a thermal degradation test on the insulating coating material containing the antioxidant (or on a cable clad with the insulating coating material), determining fracture elongations and antioxidant concentrations (residual concentrations of the functional group) at two or more time points, determining the degradation level and degradation rate of the insulating coating material, and thereby predicting a time for the fracture elongation to reach a predetermined level.

With reference to FIG. 3, according to the conventional life evaluation method, a fracture elongation test is performed at predetermined time intervals on a insulating coating material having an actual antioxidant concentration (actual-use initial concentration) in a cable clad with the insulating coating material, and data are plotted with time base to give a curve 26. When the fracture elongation of the sample abruptly decreases and falls below 100% after a lapse of, for example, about 5000 hours, this time is evaluated as the life (the end of life) of the tested insulating coating material. Thus, it takes a very long time for the conventional life evaluation method to evaluate the life of the insulating coating material.

According to the present invention, a fracture elongation test is performed on a cable insulating coating material having an antioxidant concentration lower than the actual antioxidant concentration to obtain data shown by a curve 29. The method employs not always one type of such cable insulating coating material having an initial antioxidant concentration lower than the actual-use initial antioxidant concentration and, where necessary, may employ two or more cable insulating coating materials (or cables clad with the insulating coating materials) having antioxidant concentrations lower than the actual-use initial concentration. In the sample illustrated in FIG. 3, the fracture elongation abruptly decreases at a time of about 2000 hours, and testing in further detail (collection of a multiplicity of data about the time base) may be performed in the vicinity of this time. In the sample illustrated in FIG. 3, the time of about 2000 hours at which the fracture elongation falls below 100% is determined as judgment information based on the fracture elongation.

In an embodiment of the present invention, the absorbance ratio of the radical-scavenging functional group in the antioxidant is measured at two or more time points on a cable insulating coating material having an actual-use antioxidant concentration (actual-use initial concentration) and on a cable insulating coating material having an antioxidant concentration lower than the actual-use initial concentration. Thus, data indicated by a straight line 27 and a straight line 28 are obtained for the cable insulating coating material having an actual-use initial antioxidant concentration and for the cable insulating coating material having an initial antioxidant concentration lower than the actual-use initial concentration. Test samples of the cable insulating coating material or of the cable clad with the insulating coating material are stored typically in one thermostat so as to grasp their degradation patterns under the same conditions. The test samples are held at high temperatures of, for example, 100° C. or higher, because the tests performed in the present invention are accelerated tests. As the cable insulating coating material having an initial antioxidant concentration lower than the actual-use initial concentration, it is preferred to prepare cable insulating coating material samples having not one but two or more different antioxidant concentrations lower than the actual-use initial concentration, for obtaining more precise data as described above.

The resulting data on the absorbance ratio of the radical-scavenging functional group are expected to be plotted as a downward-sloping straight line with the time base due typically to the change in molecular structure accompanied with radical scavenging. A point A at which the straight line 28 and the fracture elongation curve 29 intersect each other is determined, where the straight line 28 and the fracture elongation curve 29 are both of the cable insulating coating material having an initial antioxidant concentration lower than the actual-use initial concentration, and the point A is extended to the right in parallel with the time base (abscissa). Independently, the straight line 27 of the cable insulating coating material having the actual use antioxidant concentration is extended, and an intersecting point B at which the two extended lines intersect each other (in this sample, about 5000 hours) is defined as the life of the cable insulating coating material having the actual use antioxidant concentration. This significantly advantageously enables the evaluation of the life of the cable insulating coating material in a life test for a duration up to 2000 hours.

In this process, it is important that the straight line 27 of the absorbance ratio of the radical-scavenging functional group in the cable insulating coating material having the actual use antioxidant concentration should be parallel with the straight line 28 of absorbance ratio of the radical-scavenging functional group in the cable insulating coating material having an initial antioxidant concentration lower than the actual-use initial concentration at least until the straight line 28 reaches the intersecting point A. If either or both of the straight lines 27 and 28 cannot maintain parallelism, data on the absorbance ratio of the radical-scavenging functional group is difficult to be used for the life prediction of a cable insulating coating material, as is apparent from the above description. This may be expected to happen in some types of antioxidants. In such a case, the antioxidant concentration(s) of cable insulating coating material(s) to be prepared should be examined, because the lack in parallelism may be caused also by unsuitable setting of the concentration(s) lower than the actual-use initial concentration.

In the present invention, a fracture elongation test of a cable insulating coating material having an actual-use initial antioxidant concentration is not always essential, but there is no problem about using this as complementary data for the life prediction or life diagnosis according to the present invention.

For allowing a computer to support the testing method according to the present invention, it is effective to employ the following procedural steps:

(1) calculating the ratio of the absorbance of the functional group in the antioxidant to the absorbance of the base polymer in an infrared spectrum;

(2) calculating the rate of decrease of the functional group in the antioxidant per unit time in a plot with the abscissa indicating the degradation time and the ordinate indicating the absorbance ratio;

(3) calculating an absorbance ratio of the functional group in the antioxidant, which absorbance ratio corresponding to the life determined through the tensile test; and (4) comparing the absorbance ratio of a sample having an initial antioxidant concentration lower than the actual-use initial concentration as determined in the step (3) with the absorbance ratio of a sample containing the antioxidant in a concentration set as intended to achieve the life determined in the step (3), and, when the two absorbance ratios are equal to each other, determining that this life testing method is applicable, and calculating a time for the latter absorbance ratio to reach the concentration calculated in the step (2). In addition to these steps, the method may further include the following steps:

(5) calculating (according to the least squares method) the slope and intercept in an Arrhenius plot of lives predicted in the step (4) at two or more different accelerated thermal degradation temperatures; and (6) calculating the life at an assumed working temperature.

The present invention provides a testing method for predicting a life of a cable insulating coating material containing an antioxidant. Specifically, the testing method is suitable to be adopted to various wirings requiring a very long life typically in nuclear power plants. This contributes to improvements in reliability and safety of electric systems in the nuclear power plants.

What is claimed is:

1. A method for evaluating a life of a cable insulating coating material, the cable insulating coating material being used for covering a conductor and including a base polymer and an antioxidant having a functional group for suppressing an oxidative deteriorative reaction of the base polymer, the method comprising the steps of:

performing a thermal degradation test on a cable insulating coating material containing the antioxidant;

determining degradation levels and degradation rates of the cable insulating coating material at two or more time points in the thermal degradation test based on a ratio of an absorbance of the functional group of the antioxidant to an absorbance of the base polymer; and evaluating the life of the cable insulating coating material.

2. The method for evaluating a life of a cable insulating coating material according to claim 1, the method comprising the steps of:
performing thermal degradation tests on a cable insulating coating material containing the antioxidant in an initial concentration lower than an actual-use initial concentration and on a cable insulating coating material containing the antioxidant in the actual-use initial concentration;
determining degradation levels and degradation rates of the cable insulating coating materials containing the antioxidant in the respective concentrations based on the ratios of an absorbance of the functional group of the antioxidant in the respective concentrations to an absorbance of the base polymer; and
evaluating a life of the cable insulating coating material containing the antioxidant in the actual-use initial concentration.

3. The method for evaluating a life of a cable insulating coating material according to claim 1, wherein the antioxidant has a functional group having a radical scavenging function in a molecular structure thereof.

4. A method for evaluating a life of a cable insulating coating material, the cable insulating coating material being used for covering a conductor and including a base polymer and an antioxidant having a functional group for suppressing a deteriorative reaction of the base polymer, the method comprising the steps of:
performing a thermal degradation test on a first sample containing the antioxidant in an initial concentration lower than an actual-use initial concentration, and estimating such a critical concentration of the radical-scavenging functional group as to suppress oxidative degradation based on a correlation between a fracture elongation of the first sample in a tensile test and a peak intensity of the radical-scavenging functional group in the first sample;
performing a thermal degradation test on a second sample containing the antioxidant in the actual-use initial concentration, and estimating an initial peak intensity of the radical-scavenging functional group in the second sample and a rate of decrease of the peak intensity; and
calculating a time for the concentration of the radical-scavenging functional group in the first sample containing the antioxidant in an initial concentration lower than the actual-use initial concentration to reach the estimated critical concentration, based on the estimated initial peak intensity and rate of decrease of the peak intensity of the radical-scavenging functional group in the second sample containing the antioxidant in the actual-use initial concentration, and predicting a thermal degradation life of the cable insulating coating material at a predetermined temperature.

5. A method for testing a cable coating material to evaluate a life thereof, the cable coating material including an antioxidant having a functional group for suppressing an oxidative deteriorative reaction, the method comprising the steps of:
using means for quantitatively determining a concentration of a functional group having a radical scavenging function in a molecular structure of the antioxidant through infrared spectrophotometry;
performing a thermal degradation test on a first sample containing the antioxidant in an initial concentration lower than an actual-use initial concentration, and estimating such a critical concentration of the radical-scavenging functional group as to suppress oxidative degradation based on a correlation between a fracture elongation of the first sample in a tensile test and a peak intensity of the radical-scavenging functional group in the first sample;
performing a thermal degradation test on a second sample containing the antioxidant in the actual-use initial concentration, and estimating an initial peak intensity of the radical-scavenging functional group in the second sample and a rate of decrease of the peak intensity; and
calculating a time for the concentration of the radical-scavenging functional group in the first sample containing the antioxidant in an initial concentration lower than the actual-use initial concentration to reach the estimated critical concentration based on the initial peak intensity and the rate of decrease of the peak intensity of the radical-scavenging functional group each estimated on the second sample containing the antioxidant in the actual-use initial concentration,
and predicting a thermal degradation life of the cable insulating coating material at a predetermined temperature.

6. The method for testing a cable insulating coating material to evaluate a life thereof according to claim 5, further comprising the steps of:
collecting data of concentration distribution of the radical-scavenging functional group in a thickness direction of cable insulating coating through an infrared spectral mapping measurement of the concentration of the radical-scavenging functional group in a molecular structure of the antioxidant; and
performing estimation of the concentration and the critical concentration of the functional group also in consideration of a pattern of the concentration distribution.

7. A method for evaluating a life of a cable insulating coating material, the method comprising the steps of:
evaluating a life at an assumed working temperature through Arrhenius plotting of thermal degradation lives at two or more different temperatures; and
adopting, to all or part of the thermal degradation lives, a thermal degradation life or lives predicted by the life evaluation method of claim 5.

8. A method for evaluating a life of a cable insulating coating material, the cable insulating coating material including a base polymer and an antioxidant for suppressing an oxidative deteriorative reaction, the method comprising the steps of:
using means for quantitatively determining a concentration of a functional group having a radical scavenging function in a molecular structure of the antioxidant based on a ratio of an absorbance of the functional group to an absorbance of the base polymer each obtained through infrared spectrophotometry;
as a first stage, preparing a first sample containing the antioxidant in an initial concentration lower than an actual-use initial concentration, performing a thermal degradation test on the first sample, and estimating such a critical concentration of the radical-scavenging functional group as to suppress oxidative degradation based on a correlation between a change in fracture elongation of the first sample with a heating time, the fracture elongation being determined in a tensile test and a change in peak intensity of the radical-scavenging functional group with a heating time;
as a second stage, preparing a second sample containing the antioxidant in a concentration intended to achieve a target life, performing a thermal degradation test on the second sample, and estimating a rate of decrease of the radical-scavenging functional group;

checking that the rates of decrease of the radical-scavenging functional group estimated in the first stage and the second stage, respectively, are equal to each other;

calculating a time for the concentration of the radical-scavenging functional group in the second stage to reach the critical concentration estimated in the first stage, based on a difference in concentration of the radical-scavenging functional group between the first stage and the second stage at an identical degradation time and based on the estimated rate of decrease of the radical-scavenging functional group; and predicting a thermal degradation life of the cable insulating coating material at a temperature used in the thermal degradation test.

9. The method for evaluating a life of a cable insulating coating material according to claim 8, further comprising the steps of:

performing an infrared spectrophotometric mapping measurement of the concentration of the radical-scavenging functional group in the molecular structure of the antioxidant;

collecting data of concentration distribution of the radical-scavenging functional group in a thickness direction of cable insulating coating; and calculating the concentration of the functional group based on an average of the concentration distribution while excluding data showing an irregularity in a distribution pattern from calculations performed in the estimations of the concentration and rate of decrease of the peak intensity of the radical-scavenging functional group, and subjecting the results to the prediction of the life.

10. A method for evaluating a life of a cable insulating coating material, the cable insulating coating material including an antioxidant for suppressing an oxidative deteriorative reaction, the method comprising the steps of:

evaluating a life of the cable insulating coating material at an assumed working temperature through Arrhenius plotting of thermal degradation lives at two or more different temperatures; and adopting, to all or part of the thermal degradation lives, a thermal degradation life or lives predicted by the life evaluation method of claim 8.

11. A method for evaluating a life of a cable insulating coating material for use in a nuclear power plant, the cable insulating coating material being used for a cable in an electrical facility in the nuclear power plant and including a base polymer and an antioxidant, the antioxidant containing a functional group having a radical scavenging function, the method comprising the steps of:

using means for quantitatively determining a concentration of the radical-scavenging functional group in a molecular structure of the antioxidant based on a ratio of an absorbance of the functional group to an absorbance of the base polymer each obtained through infrared spectrophotometry;

as a first stage, preparing a first sample containing the antioxidant in a concentration lower than an actual-use initial concentration, performing a thermal degradation test on the first sample, and estimating such a critical concentration of the radical-scavenging functional group as to suppress oxidative degradation based on a correlation between a change in fracture elongation of the first sample with a heating time, the fracture elongation being determined in a tensile test and a change in peak intensity of the radical-scavenging functional group with a heating time;

as a second stage, preparing a second sample containing the antioxidant in a concentration intended to achieve a target life, performing a thermal degradation test on the second sample, and estimating a rate of decrease of the radical-scavenging functional group;

checking that the rates of decrease of the radical-scavenging functional group estimated in the first stage and the second stage, respectively, are equal to each other;

calculating a time for the concentration of the radical-scavenging functional group in the second stage to reach the critical concentration estimated in the first stage, based on a difference in concentration of the radical-scavenging functional group between the first stage and the second stage at an identical degradation time and based on the estimated rate of decrease of the radical-scavenging functional group; and predicting a thermal degradation life of the cable insulating coating material at a temperature used in the thermal degradation test.

12. The method for evaluating a life of a cable insulating coating material for use in a nuclear power plant according to claim 11, further comprising the steps of:

performing an infrared spectrophotometric mapping measurement of the concentration of the radical-scavenging functional group in the molecular structure of the antioxidant;

collecting data of concentration distribution of the radical-scavenging functional group in a thickness direction of cable insulating coating; and calculating the concentration of the functional group based on an average of the concentration distribution while excluding data showing an irregularity in a distribution pattern from calculations performed in the estimations of the concentration and rate of decrease of the peak intensity of the radical-scavenging functional group, and subjecting the results to the prediction of the life.

13. A method for evaluating a life of a cable insulating coating material for use in a nuclear power plant, the method comprising the steps of:

evaluating a life of the cable insulating coating material at an assumed working temperature through Arrhenius plotting of thermal degradation lives at two or more different temperatures; and adopting, to all or part of the thermal degradation lives, a thermal degradation life or lives predicted by the life evaluation method of claim 11.

\* \* \* \* \*